United States Patent [19]

Carrel

[11] 4,409,970
[45] Oct. 18, 1983

[54] APPARATUS AND METHOD FOR TREATMENT OF COMMINUTED COLLES' FRACTURE

[76] Inventor: Edson D. Carrel, 30 River Forest, Anderson, Ind. 46011

[21] Appl. No.: 246,151

[22] Filed: Mar. 23, 1981

[51] Int. Cl.³ .............................................. A61F 5/04
[52] U.S. Cl. ................................. 128/84 C; 128/92 A
[58] Field of Search ................ 128/87 A, 87 B, 92 B, 128/92 A, 84 R, 84 C

[56] References Cited

U.S. PATENT DOCUMENTS

| | | | |
|---|---|---|---|
| 1,933,825 | 11/1933 | Sloan | 128/84 R |
| 2,237,251 | 4/1941 | Longfellow | 128/87 A |
| 2,646,794 | 7/1953 | Baer | 128/87 A |
| 3,997,138 | 12/1976 | Crock et al. | 128/92 B |
| 4,041,939 | 8/1977 | Hall | 128/92 B |
| 4,342,309 | 8/1982 | Eftekhar | 128/84 R |

FOREIGN PATENT DOCUMENTS 350121 3/1922 Fed. Rep. of Germany ... 128/87 A

*Primary Examiner*—Kyle L. Howell
*Assistant Examiner*—C. W. Shedd
*Attorney, Agent, or Firm*—Woodard, Weikart, Emhardt & Naughton

[57] ABSTRACT

An apparatus and method for the treatment of communited Colles' fracture are described herein which include a kit comprising first and second stainless steel bone screws having self-tapping points and being about seven sixty-fourths inch in diameter. The bone screws include threaded portions of about one inch and one and one-half inches, respectively, and also include eye portions. The kit also includes a stainless steel wire bow having a pair of straight side portions and an interconnecting generally V-shaped intermediate portion. The surgical kit further includes an elongated, elastic material for connection between the intermediate portion of the wire bow and one of the bone screws to apply a traction force for facilitating healing of the fracture. Also disclosed herein is a method for the treatment of a Colles' fracture which includes closed reduction of the fracture, insertion of a first bone screw into the second metacarpal and a second bone screw into the ulna adjacent the elbow, applying a plaster cast to the patient's forearm incorporating the ulnar bone screw incorporating a wire bow into the cast, and connecting an elastic material between the wire bow and the metacarpal bone screw to apply a traction force on the metacarpal bone screw.

10 Claims, 10 Drawing Figures

APPARATUS AND METHOD FOR TREATMENT OF COMMINUTED COLLES' FRACTURE

BACKGROUND OF THE INVENTION

1. Field of the Invention

The present invention relates to the field of apparatus and methods for the treatment of fractures, and more particularly to an apparatus and method providing a portable, dynamic traction assembly for the treatment of a fracture.

2. Description of the Prior Art

There have been a great number and variety of methods and apparatus for the treatment of bone fractures, many of these being specialized for the treatment of particular fracture sites and types. The proper setting of a fracture to provide proper healing and rejoining of the bone sections frequently employs a pin or other artificial device to be achored into the bone sections so that the tendency of the sections to remain apart or misaligned can be overcome. While certain fractures can be treated simply with an externally applied, plaster cast, others require the use of pins to assure proper alignment of the bone sections.

The present invention relates to the treatment of a fracture of the distal radius, known more particularly as a Colles' fracture. It has been recognized that the pull of the long flexor and extensor tendons which extend to the fingers and thumb apply a compressive force in the area of a Colles' fracture, and this will interfere with the proper loction and healing of the bone fragments unless offset. Consequently, various methods of treatment have been employed which attempt to offset these forces, while other methods and apparatus simply ignore the forces.

Methods which have been conceived to offset these compressive forces of the flexor and extensor tendons have taken several forms. One approach is to hospitalize the patient and to apply skeletal traction by a system of weights and pulleys following reduction of the fracture. This technique is of course very inconvenient and expensive for the patient. Another approach has been to reduce the fracture and to insert pins through a metacarpal distal to the fracture and through the ulna proximal to the fracture, with both of these pins being incorporated into a plaster cast for rigid fixation. This procedure has the disadvantage of allowing less exercise of the fingers due to the restrictions of the cast and pins, and does not provide any dynamic elastic forces to counterbalance the forces of the tendons.

Another method of pin fixation has been provided by the use of various devices. Typically, these devices involve the placement of a first pin in a metacarpal distal to the fracture and a second pin in the radius proximal to the fracture. The pins are then connected by a device which spans therebetween, and the relationship between the pins is either a rigid fixation or a fixation providing for limited pivoting movement. An example of such a device is contained in U.S. Pat. No. 1,789,060, isued to Weisenbach on Jan. 13, 1931. This patent shows a clamp for a bone fracture in which several pins are anchored into the bone sections on opposite sides of the fracture. The pins are connected by clamps which are joined pivotally to permit relative movement between the pins on opposite sides of the fracture. Similar such devices providing for rigid fixation by interconnection of pins mounted on opposite sides of the fracture, and typically involving compressive forces to maintain the fracture in place, are disclosed in the following U.S. Pat. Nos. 583,455, issued to Bush on June 1, 1897; 1,201,884, issued to Overmeyer on Oct. 17, 1916; 2,333,033, issued to Mraz on Oct. 26, 1943; 3,244,170, issued to McElvenny on Apr. 5, 1966; 3,835,849, issued to McGuire on Sept. 17, 1974; and 3,862,631, issued to Austin on Jan. 28, 1975.

In U.S. Pat. No. 2,091,643, issued to Longfellow on Aug. 31, 1937, there is shown a surgical counter traction splint which includes pins or wires extending through the bones of a limb and applying pressure to extend the bones in a traction manner. The Longfellow device is a fairly complicated one involving several sliding and threaded elements connected together. A similar type of apparatus is shown in each of U.S. Pat. Nos. 2,035,952, issued to Ettinger on Mar. 31, 1936, and 2,024,325, issued to Allen on Dec. 17, 1935. Other devices of only general interest which are intended for locating the relative placement of fractured bones to permit healing are disclosed in U.S. Pat. Nos. 1,933,825, issued to Sloan on Nov. 7, 1933; 4,102,339, issued to Weber et al. on July 25, 1978; 3,877,424, issued to Murray on Apr. 15, 1975; and 1,662,758, issued to Nicholson et al. on Mar. 13, 1928.

In an article entitled "Skeletal Traction Methods" by Mays et al. appearing in *Clinical Orthopaedics and Related Research*, Vol. 102, July–August 1974, p. 144–151, there is described a method for the treatment of a comminuted intra-articular fracture of the distal radius which includes a traction technique employing a bow secured within a plaster cast mounted on the forearm. The Mays et al. technique is similar to that of the present invention in that it does employ bone screws mounted to the second metacarpal and also to the ulna, mounts a plaster cast on the person's forearm and secures a wire bow in the cast, and then attaches a rubber band between the bow and the metacarpal pin to apply the traction force. However, the Mays et al. technique is only generally described, with no details given as to the particular materials and their configurations as used in the technique.

Also of interest to the present invention are the following patents. In U.S. Pat. No. 2,485,531, issued to Dzus et al. on Oct. 18, 1949, there is described a surgical toggle bolt used in bone fixation and which includes a J-shaped member to operate as a handle for turning the device. A hip joint prosthesis and associated bone screw are described in U.S. Pat. No. 3,781,917, issued to Mathys on Jan. 1, 1974. The Mathys bone screw is typical of prior art bone screws and includes a grooved head to receive a screwdriver. A different type of bone screw is disclosed in the Bush patent, U.S. Pat. No. 583,455, issued on June 1, 1897. The Bush bone screw includes a thumb-nut or wing-nut secured at one end to assist in manipulation of the screw. In U.S. Pat. No. 4,037,592, issued to Kronner on July 26, 1977, there is disclosed a guide pin locating tool and method for guiding a bone screw during placement within a bone.

It has also been indicated that certain techniques for treatment of a Colles' fracture have failed to take into account the disadvantages associated with the elastic compression forces applied across the fracture area by the long flexor and extensor tendons to the fingers and thumb. These forces tend to deform the fracture reduction and frequently cause loss of position of the fracture fragments. One method of treatment along these lines has been simply a closed reduction of the fractures and an application of a cast to immobilize the fracture. In practice, it is typically observed after a few weeks that there is a gradual loss of position of the bone fragments as exercises of the fingers and thumb are done in the initial period of healing.

SUMMARY OF THE INVENTION

Briefly described in one aspect of the present invention, there is provided a surgical kit for providing a portable, dynamic traction assembly for the treatment of a communited Colles' fracture, which kit includes stainless steel bone screws having self-tapping points and being about seven sixty-fourths of an inch in diameter, a stainless steel wire bow having a pair of straight side portions and a generally V-shaped intermediate portion extending therebetween, and an elongated, elastic material for connection between the intermediate portion of the wire bow and one of the screws when in place. In another aspect, the present invention provides a method for the treatment of a Colles' fracture, and also a bone screw particularly adapted for use in this method.

DESCRIPTION OF THE PREFERRED EMBODIMENT

Figure 1:
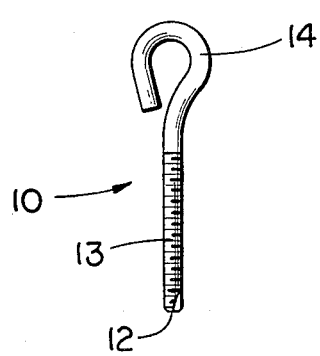
FIG. 1 is a plan view of a bone screw useful in accordance with the present invention.
Figure 2:
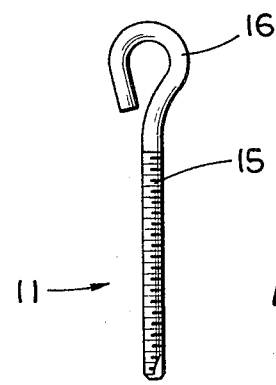
FIG. 2 is the plan view of a second embodiment of a bone screw useful in accordance with the present invention.
Figure 3:
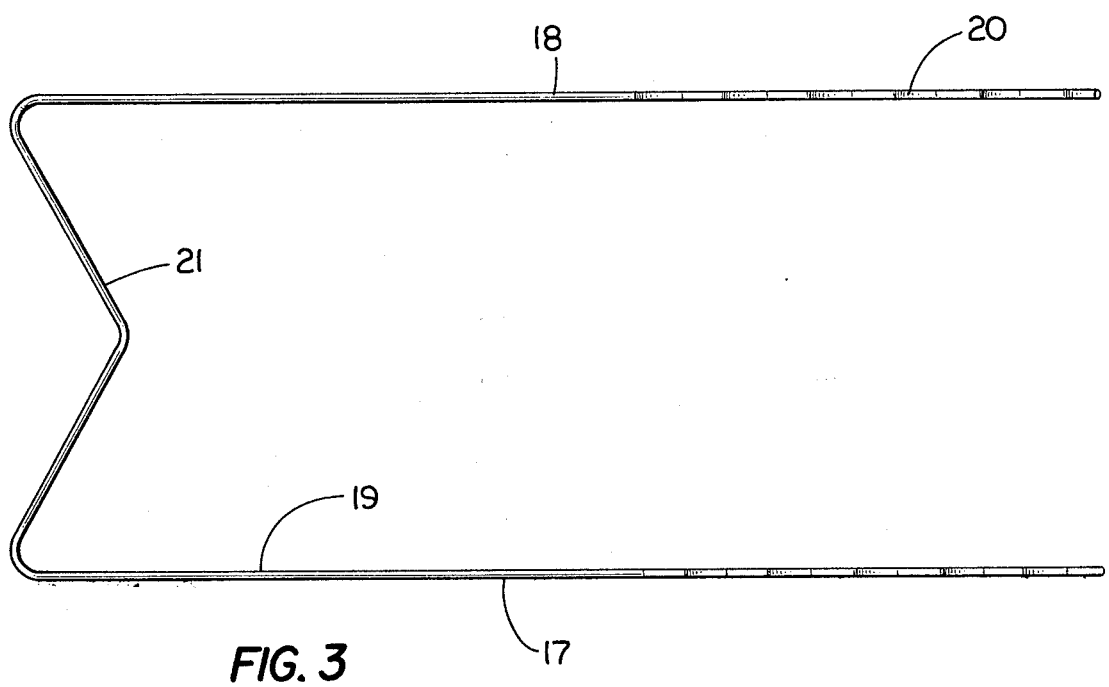
FIG. 3 is a plan view of a wire bow useful with the present invention.
Figure 4:
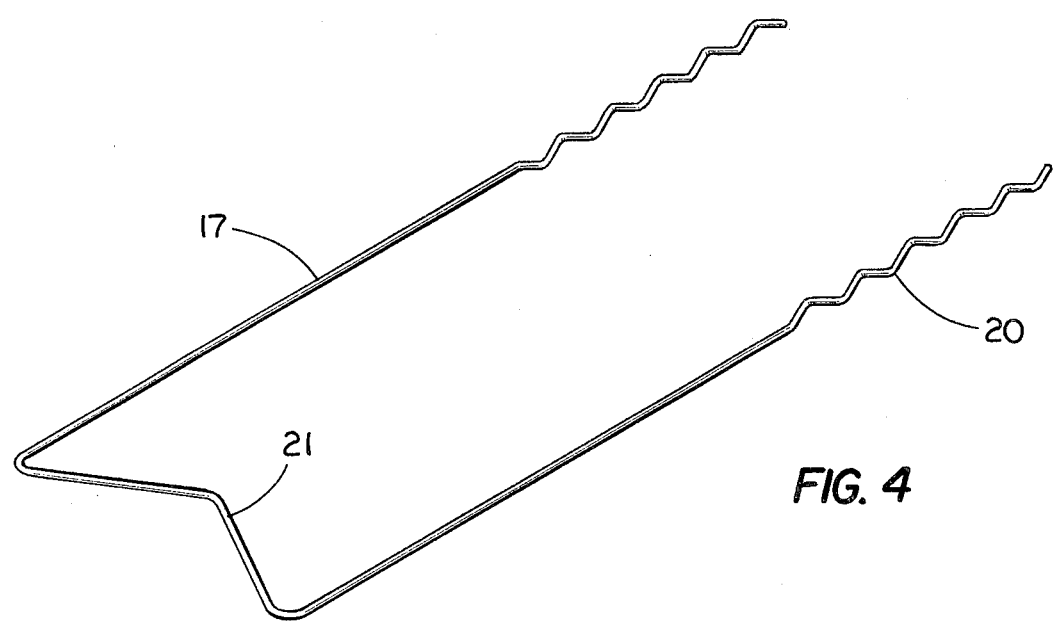
FIG. 4 is a perspective view of the wire bow of FIG. 3.
Figure 5:
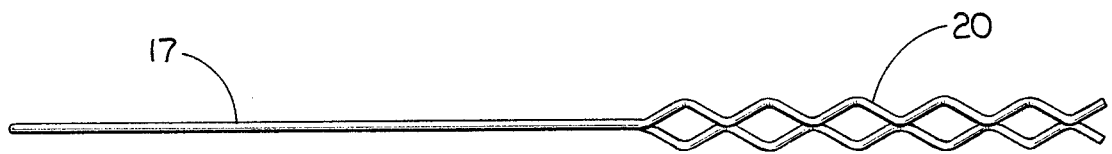
FIG. 5 is a side, elevational view of the wire bow of FIG. 3.
Figure 6:
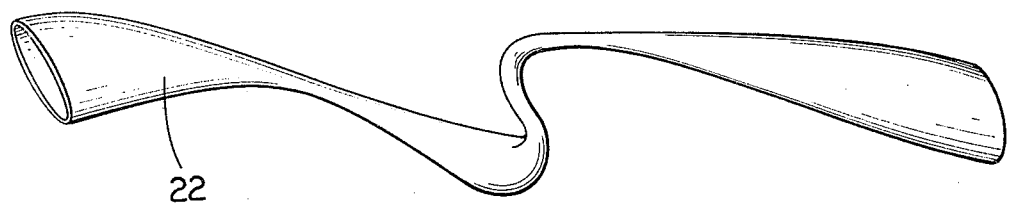
FIG. 6 is a perspective view of a piece of elastic material useful with the present invention.
Figure 7:
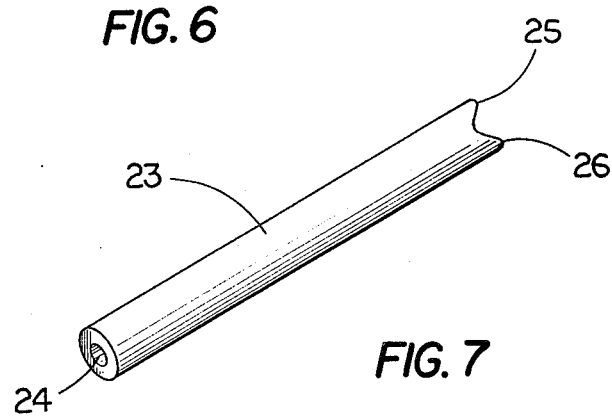
FIG. 7 is a perspective view of a drill guide useful with the present invention.
Figures 8, 9:
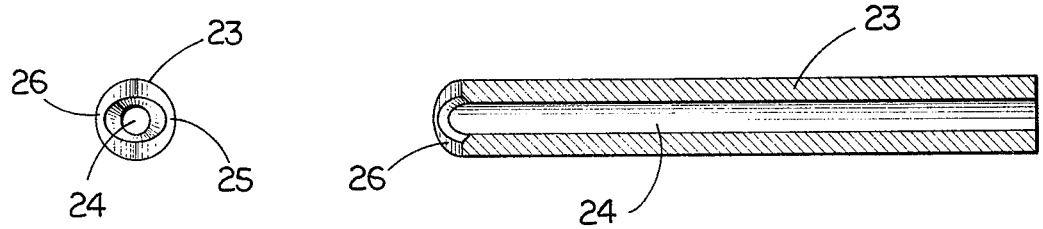
FIG. 8 is an end, elevational view of the drill guide of FIG. 7.
FIG. 9 is a side, cross-sectional view of the drill guide of FIG. 7.
Figure 10:
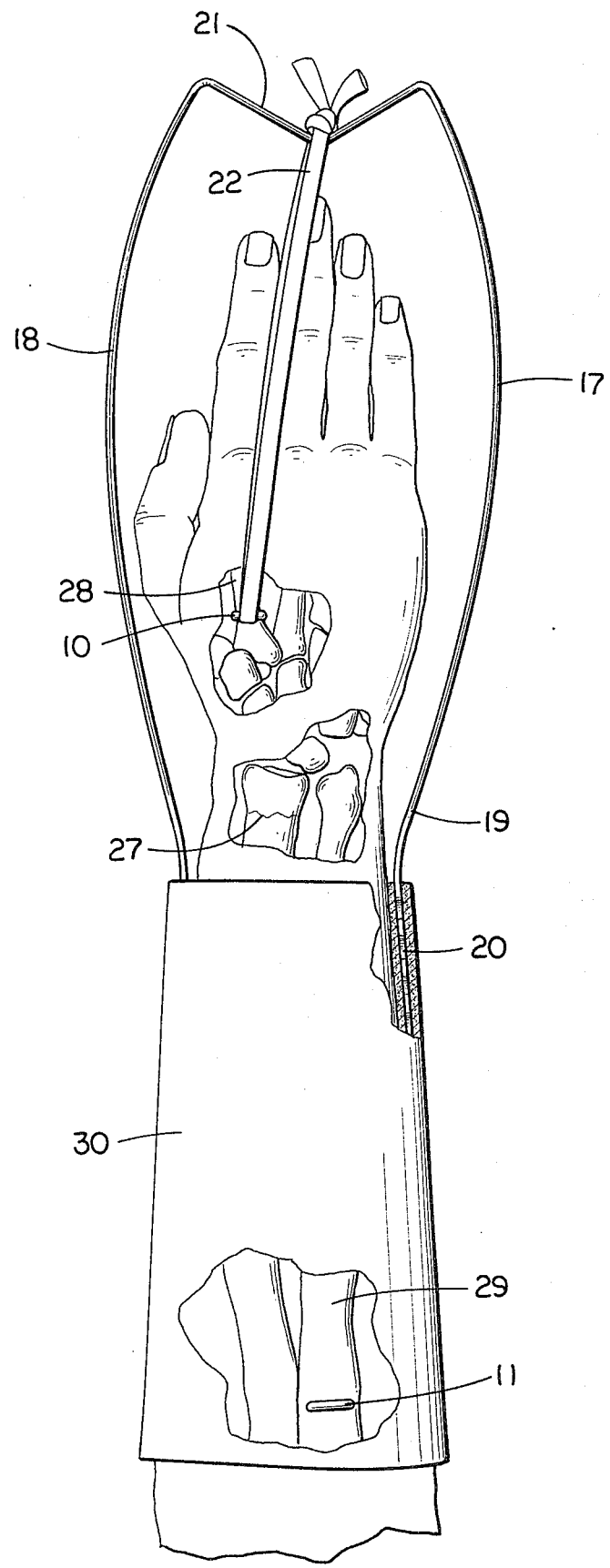
FIG. 10 is a plan view of the traction assembly as used in the treatment of Colles' fracture according to the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In one aspect of the present invention, there is provided a surgical kit useful in establishing a portable, dynamic traction assembly for treatment of a communited Colles' fracture. The surgical kit includes a pair of stainless steel bone screws 10 and 11 having self-tapping points, such as 12, and being about seven sixty-fourths inch in diameter. One of the bone screws 10 preferably has a threaded portion 13 about 1 inch in length and an eye portion 14. The other bone screw 11 preferably has a threaded portion 15 about one and one-half inches in length and also an eye portion 16. These bone screws are especially adapted for insertion into the second metacarpal and the ulna, respectively, as will be more fully set forth herein. The stainless steel composition of the bone screws is non-reactive to the body, and is therefore desirable. As will be further described, the self-tapping point is desirable since it means that the threads for the screw do not have to be cut with a tap.

The eye portion of the screw, as opposed, for example, to the typical slot at the end of a bone screw, is advantageous since it facilitates turning the screws by hand for insertion into the bones, and also facilitates use of the screws in the method also described herein. In one application, the eye is desirable since it facilitates the tying of a tensioning member to the bone screw, and in another instance is desirable since it facilitates incorporation of the bone screw into a sleeve cast to fix the cast in relationship to a patient's forearm.

The surgical kit of the present invention also includes a stainless steel wire bow 17 which has a pair of straight side portions 18 and 19 having first and second ends. The first ends of the side portions of the bow include a plaster-attaching configuration, such as shown at 20, such as the wavy portion shown in the drawings. This configuration facilitates securement of the first ends of the side portions into a cast fitted to a person's forear. The wire bow further includes a generally V-shaped intermediate portion 21 extending between the second ends of the side portions.

The surgical kit of the present invention further includes an elongated, elastic material 22 for connection between the center of the intermediate portion of the wire bow and one of the bone screws. This material could be of several different varieties which would have the flexibility needed for mounting in the manner to be described, and also which would have sufficient strength and elasticity to apply the desired traction forces. In a particularly preferred embodiments, the elastic material comprises hollow tubing having a diameter of about three-fourths of an inch.

The surgical kit also desirably includes a drill guide for facilitating the drilling of holes in the bone to accommodate the bone screws. The drill guide 23 includes a hollow center 24 and at one end has a pair of tips 25 and 26 to help steady the guide on the bone. For the indicated bone screws, it is desirable that the drill guide be adapted for use in drilling a hole having a diameter of about seven sixty-fourths of an inch. It is also desirable that the surgical kit include an instruction sheet containing a summary of the steps followed in using the components of the surgical kit.

In another aspect, the present invention provides a method for treating the comminuted Colles' fracture 27 of a patient by providing a portable, dynamic traction assembly. The method involves the initial step of making a closed reduction of the patient's fracture under suitable anesthesia, followed by suspending the patient's forearm in a generally vertical position. The suspension of the forearm preferably includes the use of finger traps and a counterbalance weight of about ten pounds. The hand and forearm are then prepared with aseptic technique and the forearm is draped with a sterile towel.

Stab incisions are then made over the base of the second metacarpal shaft 28 in the back of the hand and also over the proximal ulnar shaft 29 over the subcutaneous border of the ulna adjacent the elbow. Holes are then drilled through the second metacarpal and the ulna through both cortices with a drill of about seven sixty-fourths of an inch diameter. Preferably, the described drill guide 23 is employed to assure proper location of the drill to the bone, and particularly to avoid the drill point from wandering from the initial placement. The use of such drill guides and the procedure of making a hole in the bones is well known in the prior art, and therefore is not described in detail herein or shown in the drawings. Briefly, the drill guide is positioned with the spaced-apart points 25 and 26 staddling the bone and maintaining the position of the guide with respect to the bone while the drill is inserted through the guide and applied to the bone.

A first bone screw 10 having a threaded portion 13 of about one inch in length is inserted into the second metacarpal 28 into both cortices, and a second screw 11 having a threaded portion 15 of about one and one-half inches in length is inserted into the ulna 29 adjacent the patient's elbow through both cortices. The bone screws are as described previously with respect to the surgical kit of the present invention. The incisions are then closed around the screws with interrupted sutures.

A well padded, short arm cast 30 is applied onto the patient's forearm, and incorporating the ulnar bone screw. As suggested previously, the ulnar bone screw desirably includes an eye portion which is readily incorporated into the arm cast and which fixes the position of the cast with respect to the patient's forearm. This will permit the application of traction forces in the manner below described. The cast extends to about two to three inches above the wrist, and preferably includes twice the usual webril padding to prevent pressure sores.

While the plaster is setting up, post-reduction x-rays are desirably taken to assure the continued proper relationships of the bone fragments. A wire bow 17 is then incorporated into the cast 30 surrounding the hand by the use of additional plaster. The wire bow is as previously described with respect to the surgical kit, and the plaster-attaching first ends 20 of the side portions 18 and 19 of the bow are secured within the cast. The elongated, elastic material 22, previously described, is then connected between the center of the intermediate portion 21 of the wire bow 17 and the eye 14 of the metacarpal bone screw 10 to apply traction force on the first screw 10. The elastic material 22 may be conveniently applied by threading it through the eye 14 of the metacarpal bone screw and then tying it over the center of the V-shaped portion 21 of the wire bow. A tension force of preferably from about seven to about ten pounds is applied by use of the elastic material.

The finger traps are then removed and the hand is preferably maintained in elevation for about seventy-two hours after connection of the elastic material to minimize swelling. The traction assembly is maintained on the forearm for about eight weeks, with x-rays preferably being taken at 1, 3, 5 and 8 weeks after reduction to assure continued proper positioning of the bone fragments. The patient is encouraged during the eight week period to exercise the hand and fingers.

As a result of the use of the surgical kit of the present invention in the method described, a treatment for a communuted Colles' fracture is obtained which overcomes disadvantages previously associated with certain of the prior art devices and methods. In particular, good mobility, and therefore the possibility of exercise, is achieved by this approach while maintaining excellent fracture position. The traction forces obtained operate to counteract the undesirable forces otherwise presented by the flexor and extensor tendons extending to the fingers and thumb.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A surgical apparatus for providing a portable, dynamic traction assembly for treatment of a comminuted Colles' fracture which comprises:
   a cast received over a patient's forearm;
   a pair of first and second, stainless steel bone screws having self-tapping points and being about seven sixty-fourths of an inch in diameter, said first screw having a threaded portion about one inch in length and having an eye portion, said second screw having a threaded portion about one and one-half inches in length, said first and second bone screws being for insertion into the second metacarpal and the ulna, respectively, said second bone screw being incorporated within said cast;
   a stainless steel wire bow having a pair of straight side portions having first and second ends, each of the first ends of the side portions including a plaster attaching configuration to facilitate securement of the first ends into a cast fitted to a person's forearm, said bow further including a generally V-shaped intermediate portion extending between the second ends of the side portions; and
   an elongated, elastic material for connection between the center of the intermediate portion of said wire bow and said first bone screw.

2. The apparatus of claim 1 and which further includes a drill guide means for facilitating the drilling of holes in bone to accommodate said bone screws.

3. The apparatus of claim 2 in which said second bone screw further includes an eye portion.

4. The apparatus of claim 3 in which said elastic material comprises hollow tubing having a diameter of about three-fourths of an inch.

5. The method for treating a communuted Colles' fracture of a patient by provision of a portable, dynamic traction assembly which comprises the steps of:
   a. making a closed reduction of the patient's fracture under anesthesia;
   b. suspending the patient's forearm in a generally vertical position;
   c. preparing the hand and forearm with aseptic technique and draping the forearm with a sterile towel;
   d. making stab incisions over the base of the second metacarpal shaft in the back of the hand and also over the proximal ulnar shaft over the subcutaneous border of the ulna adjacent the elbow;
   e. drilling the second metacarpal and the ulna through both cortices with a drill of about seven sixty-fourths of an inch in diameter;
   f. inserting a first bone screw into the second metacarpal and a second bone screw into the ulna adjacent the patient's elbow, the bone screws being stainless steel, self-tapping and about seven sixty-fourths of an inch in diameter, said first bone screw having a threaded portion about one inch in length and having an eye portion, said second screw having a threaded portion about one and one-half inches in length;

g. closing the incisions around the bone screws;

h. applying a short, well-padded, cylindrical plaster cast to the patient's forearm incorporating the second bone screw and extending to about two to three inches above the wrist;

i. incorporating into the cast a stainless steel wire bow having a pair of straight side portions having first and second ends, each of the first ends of the side portions including a plaster attaching configuration to facilitate securement of the first ends into the cast the bow further including a generally V-shaped intermediate portion extending between the second ends of the side portions, said incorporating including securing the plaster-attaching first ends of the side portions within the cast; and j. connecting an elongated, elastic material between the center of the intermediate portion of the wire bow and the eye of the first bone screw to apply a traction force on the first bone screw.

6. The method of claim 5 in which step j. comprises applying a force of from about seven to about ten pounds.

7. The method of claim 5 and which further includes, after step j., the step of maintaining elevation of the patient's arm for about seventy-two hours after completion of step j. to minimize swelling.

8. The method of claim 6 in which the second bone screw further includes an eye portion and step h. comprises incorporating the eye portion of the second bone screw into the cast.

9. The method of claim 7 and which further includes, after step h., the step of taking post-reduction x-rays of the fracture.

10. The method of claim 8 in which the elastic material comprises hollow tubing having a diameter of about three-fourths of an inch.

* * * * *